United States Patent [19]

Shimizu et al.

[11] Patent Number: 5,674,678
[45] Date of Patent: Oct. 7, 1997

[54] PROCESS FOR CONTROLLING CULTURES OF RECOMBINANTS

[75] Inventors: Norio Shimizu; Yoji Odawara, both of Hitachi; Kiyoshi Fujiwara, Kudamatsu; Keiko Masuda, Nakagyo-ku; Toshiharu Kurihara, Toyonaka, all of Japan

[73] Assignee: Hitachi, Ltd., Tokyo, Japan

[21] Appl. No.: 205,603

[22] Filed: Jun. 2, 1988

Related U.S. Application Data

[63] Continuation of Ser. No. 746,795, Jun. 20, 1985, abandoned.

[30]  Foreign Application Priority Data

Jun. 22, 1984 [JP] Japan ................... 59-127472
Sep. 14, 1984 [JP] Japan ................... 59-191603

[51] Int. Cl.⁶ ......................... C12Q 1/68; C12N 9/38
[52] U.S. Cl. ........................................ 435/6; 435/207
[58] Field of Search ................... 435/69.1, 69.7, 435/71.2, 172.3, 320, 249, 6, 207; 935/29, 41, 43

[56]  References Cited

U.S. PATENT DOCUMENTS 3,912,585 10/1975 Iijima et al. ................... 435/249
4,551,433 11/1985 DeBoer ......................... 435/253
4,891,310 1/1990 Shimizu et al. ................. 435/3

FOREIGN PATENT DOCUMENTS 0036776 9/1981 European Pat. Off. ........ C12N 15/00
0136907 4/1985 European Pat. Off. ........ C12N 15/00

OTHER PUBLICATIONS

"High Density Cultivation of Biomass in Fed–Batch System with DO–Stat" by Mori, et al., Journal of Chemical Engineering of Japan, vol. 12, 1979, pp. 313–319.

Primary Examiner—James Ketter
Attorney, Agent, or Firm—Fay, Sharpe, Beall, Fagan, Minnich & McKee

[57]  ABSTRACT

Expression of a desired gene and production of a product from the desired gene can be obtained effectively by cultivating a microorganism containing a hybrid plasmid comprising the desired gene, a vector and a promoter in its cell, and adding an inducer and a nutriment simultaneously to the culture medium at the time when the nutriment originally present in the culture medium is almost consumed.

6 Claims, 8 Drawing Sheets

FIG. 2

5'
CTCAAGGCGCACTCCCGTTCTGGATAATGTTTTTTGCGCCGACATCATAA

TaqI
                                            ↓
CGGTTCTGGCAAATATTCTGAAATGAGCTGTTGACAATTAATCATCGAAC

HpaI    RsaI                       TaqI
↓  PB  ↓                   SD  ↓   Leader
TAGTTAACTAGTACGCAAGTTCACGTAAAAAGGGTATCGACAATGAAAGC
                                             MetLysAl peptide   RsaI
            ↓
AATTTTCGTACTGAAAGGTTGGTGGCGCACTTCCTGAAACGGGCAGTGTA
aIlePheValLeuLysGlyTrpTrpArgThrSer

TTCACCATGCGTAAAGCAATCAGATACCCAGCCCGCCTAATGAGCGGGCT

SD      trp E polypeptide
TTTTTTTGAACAAAATTAGAGAATAACAATGCAAACACAAAAACCGACTG
                                MetGlnThrGlnLysProThrG EcoRI
↓       3'
GAATTCTC
lyIleLeu

PROCESS FOR CONTROLLING CULTURES OF RECOMBINANTS

This is a continuation of application Ser. No. 746,795 filed on Jun. 20, 1985, now abandoned.

BACKGROUND OF THE INVENTION

This invention relates to a process for effectively cultivating microorganisms containing hybrid plasmids so as to produce a product from the hybrid plasmids in large amounts.

Recently, there has been developed a gene recombination technique for producing a large amount of a useful substance by using a host microorganism containing a hybrid plasmid obtained by inserting a gene having information for producing the useful substance into a vector plasmid of the host microorganism. By this technique, human interferon, insulin, etc. have been produced. As the host microorganism, *Escherichia coli* is generally used.

But a process for industrially producing the desired product in large amounts by using a host microorganism maintaining the desired gene has not been developed. Thus, a process for cultivating effectively the microorganism harboring hybrid plasmids has been sought by the industry.

SUMMARY OF THE INVENTION

It is an object of this invention to provide a process for controlling effectively the culture of a microorganism harboring hybrid plasmids.

This invention provides a process for controlling the culture of a microorganism containing a hybrid plasmid having a desired gene, a vector and a promoter in its cell and having the ability to express the desired gene so as to express the desired gene and harvest a product therefrom, which comprises supplying the hybrid plasmid-containing microorganism to a culture medium for culture, and adding an inducer and a nutriment simultaneously to the culture medium at the time when the nutriment originally present in the culture medium is almost consumed.

BRIEF DESCRIPTION OF THE DRAWINGS

FIG. 2 shows a base sequence at the downstream region of a trp promoter.

DESCRIPTION OF THE PREFERRED EMBODIMENTS

The promoter utilized in the present cultivation process for expressing the desired gene, can be either a trp (tryptophan) promoter, a lac promoter (Nature, 281, pp 544–548, 1979), a tac promoter (Proc. Natl. Acad. Sci. USA, 80, pp 21–25, 1983), etc.

Figure 1:
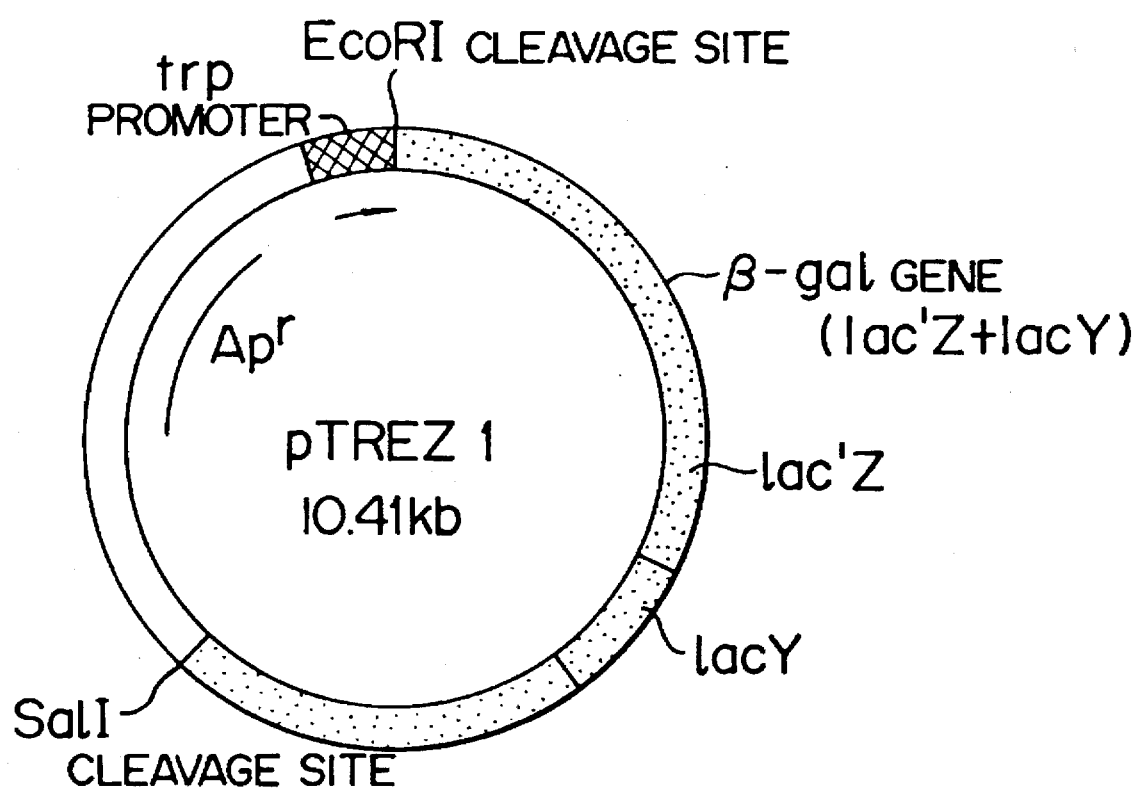
FIG. 1 shows a structure of hybrid plasmid pTREZ1.

The hybrid plasmid utilized in the present cultivation process, i.e. plasmid pTREZ1 having the structure as shown in FIG. 1, can be obtained by ligating a trp promoter and β-galactosidase gene. More particularly, hybrid plasmid pTREZ1 can be obtained from plasmid pTRE1 and plasmid pMC1403 by the process set forth below.

The plasmid pTRE1 containing a trp promoter can be obtained by inserting a DNA fragment of about 500 bp (base pairs) containing a promoter of trp operon of *E. coli*, trp L (leader peptide) and a part of end portion of trp E (anthranilate synthase) into the EcoRI site of plasmid pBR322 (Gene, 29, pp 41–49, 1984). The direction of trp promoter is the direction of $Tc^r$ (a tetracycline resistance gene) of pBR322. The EcoRI site on the upstream side of trp promoter is filled with DNA polymerase I so as to improve only the EcoRI site on the downstream of the promoter. FIG. 2 shows the base sequence in the trp promoter downstream region. By connecting a foreign gene at the EcoRI site in trp E polypeptide gene, it is possible to express the foreign gene in the form fused with 8 amino acids at the N-terminal side of trp E polypeptide.

On the other hand, the β-galactosidase gene, can be obtained from plasmid pMC1403 (J. Bacteriol, 143, pp 971–980, 1980) which has a βgalactosidase gene (lac Z+lac Y) of 6.2 kb (kilobase pairs) inserted between the EcoRI site and the SalI site.

Figure 3:
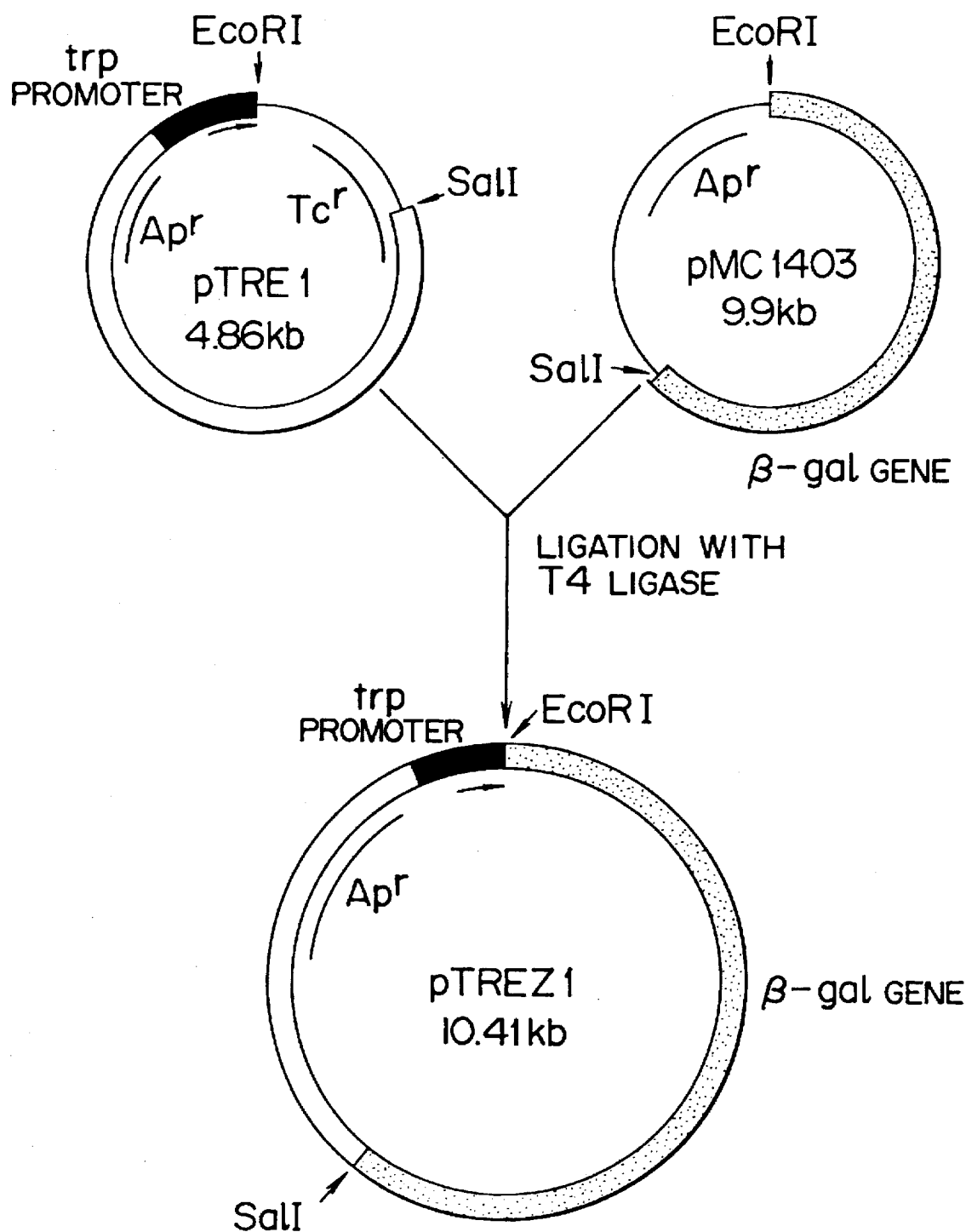
FIG. 3 is a flow diagram showing the construction of hybrid plasmid pTREZ1.

FIG. 3 shows a process for constructing plasmid pTREZ1 wherein the β-galactosidase gene from plasmid pMC1403 is inserted into the EcoRI site on pTre. The hybrid plasmid pTREZ1 of 10.21 kb can be constructed by ligating the DNA fragment of 4.21 kb containing the trp promoter cut from the plasmid pTRE1 and the β-galactosidase gene of 6.2 kb cut from the plasmid pMC1403 with $T_4$ DNA ligase.

The microorganism utilized in the present cultivation process for harboring the hybrid plasmid having a desired gene, a vector and a promoter in its cell and having the ability to express the desired gene, are various types of *E. coli*, e.g. M182, HB101, C600, X1776, DH1, etc. Among them, a recombinant for producing β-galactosidase obtained by introducing the hybrid plasmid pTREZ1 having the structure mentioned above into *E. coli* M182 which is a strain lacking in β-galactosidase gene on a chromosome (deposited in the FRI as FERM BP-816) and a recombinant for producing β-glactosidase obtained by introducing the hybrid plasmid pTREZ1 into *E. coli* HB101 (deposited in the FRI as FERM BP-815) are used the control of trp promoter and can produce β-galactosidase in a remarkably larger amount than known methods by effectively applying the function of the promoter.

Microorganisms other than *E. coli* such as yeast, *Bacillus subtilis*, etc. can also be used as the host microorganism, when suitable promoters are used and desired genes are introduced thereinto.

According to this invention, the microorganism containing a hybrid plasmid having a desired gene, a vector and a promoter in its cell and having the ability to express the desired gene, for example, a microorganism for producing β-galactosidase, is used for expressing the desired gene so as to produce its product, for example, β-galactosidase, with high efficiency. In order to control the culture of the recombinant, the recombinant is supplied to a culture medium for cultivation, and an inducer and a nutriment are added to the culture medium simultaneously at a time when the nutriment in the culture medium is almost consumed.

The inducer utilized in the present cultivation process can be either 3-β-indolylacrylic acid (IA) for the trp promoter, isopropyl-β-D-thiogalactoside (IPIG) for the lac promoter and tac promoter, etc.

The nutriment utilized in the present cultivation process can be either casamino acid (which is a mixture of amino acids), amino acids other than tryptophan, yeast extract, and a mixture thereof. Among them, the use of casamino acid is preferable.

The time when almost all of the nutriment in the culture medium is consumed can be determined when either the microorganism concentration shows a maximum value, the concentration of glucose becomes almost zero, and/or when the concentration of dissolved oxygen (DO) in the culture medium is changed from a decrease to an increase, and the like.

In the case of the hybrid plasmid containing a trp promoter, it is known that the gene is expressed by adding 3-β-indolylacrylic acid (IA), as the inducer, to during the culture (Nature, vol. 291, pp 503–506, 1981). That is, since a repressor which suppress the transcription of the gene is inactivated by IA, the synthesis of mRNA by RNA polymerase begins.

In the case the trp promoter, when the inducer IA is added, the promoter begins to function. Therefore, it is very important in the production of the product of the desired gene when the inducer should be added. As to the time of addition of IA, a method of adding IA at one hour from the beginning of the culture is disclosed in Nature, vol. 291, pp. 503–506, 1981, and a method of using the microorganism concentration as an indicator is disclosed in Japanese Patent Unexamined Publication No. 141796/83. But these methods are insufficient for industrial culture.

One method of this invention is to add the inducer such as IA using the change of DO (i.e. dissolved oxygen) concentration as an indicator in order to make possible the addition of the inducer suitable for physiologically active state of the microorganism.

When microorganisms are cultivated under constant conditions of agitation speed and air flow rate, the DO concentration decreases with the multiplication, and thus the glucose concentration in a substrate decreases due to the consumption by the microorganisms. Then, there takes place a rapid increase in the DO concentration at the time when the substrate is consumed. When the inducer such as IA and a nutriment which can be a synthesis material for the desired product such as β-galactosidase are added simultaneously to the culture medium at the time when the substrate is consumed, the desired product such as β-galactosidase can be produced in large amounts. That is, by the addition of IA and the nutriment at the time of termination of multiplication of the microorganism due to the consumption of substrate, it becomes possible to begin the production of β-galactosidase at the maximum microorganism concentration.

Figure 4:
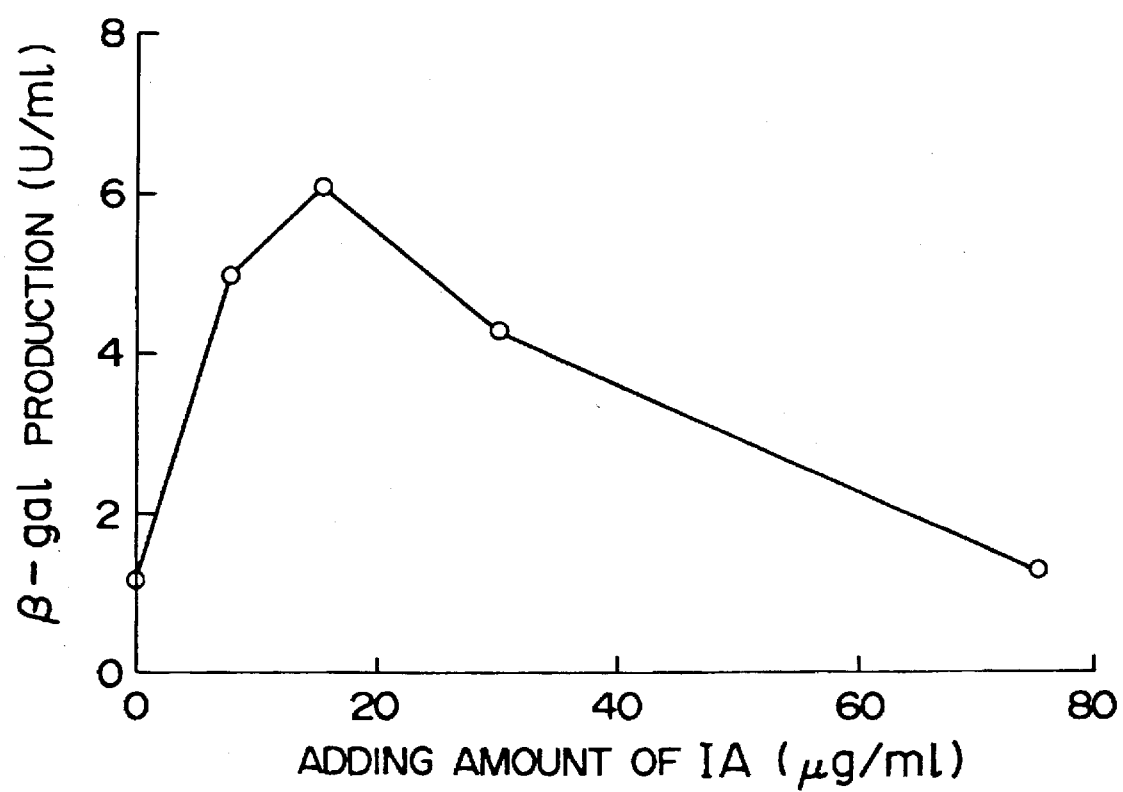
FIG. 4 is a graph showing a relationship between the adding amount of IA and the β-galactosidase produced amount.

The amount of the inducer to be added together with the nutriment is preferably 10 to 30 μg/ml, more preferably 15 μg/ml. FIG. 4 shows a relationship between the amount of β-galactosidase produced and the amount of IA added. As is clear from FIG. 4, the best result is obtained when 15 μg/ml of IA is added. This means that the addition of 10 to 30 μg/ml of IA together with the nutriment during the culture gives satisfactory results.

As the nutriment, casamino acid is most effective nutriment as shown in Table 1. When glucose is used, the production of β-galactosidase is lowered. Since casamino acid is a mixture of amino acids, the same results can be obtained by adding amino acids other than tryptophan (e.g. glycine, glutamic acid, alanine, etc.) or a mixture thereof. The amount produced increases when a larger amount of casamino acid is added, but it requires a longer culture time.

TABLE 1

| | Adding substance | | | β-Galalctosidase produced amount | |
|---|---|---|---|---|---|
| Run No. | IA (μg/ml) | Casamino acid (mg/ml) | Glucose (mg/ml) | U/ml | Ratio |
| 1 | 15 | — | — | 5.8 | 1 |
| 2 | 15 | 2.5 | — | 12.9 | 2.2 |
| 3 | 15 | — | 5 | 6.0 | 1.0 |
| 4 | 15 | 2.5 | 5 | 8.3 | 1.4 |

In the above, the explanation was made as to the hybrid plasmid containing a trp promoter, but the same thing can be applied to the case of hybrid plasmids containing a tac promoter or a tac promoter and isopropyl-β-D-thiogalactoside (IPTG) being added as an inducer.

The above-mentioned culture controlling process, that is, a process for increasing the production of a product produced by a desired gene by adding an inducer and nutriment simultaneously to the culture medium at the time when the dissolved oxygen (DO) concentration of the culture medium increases is not known in conventional culture processes of recombinants and ordinary microorganisms, and is found for the first time by the present inventors.

Figure 5:
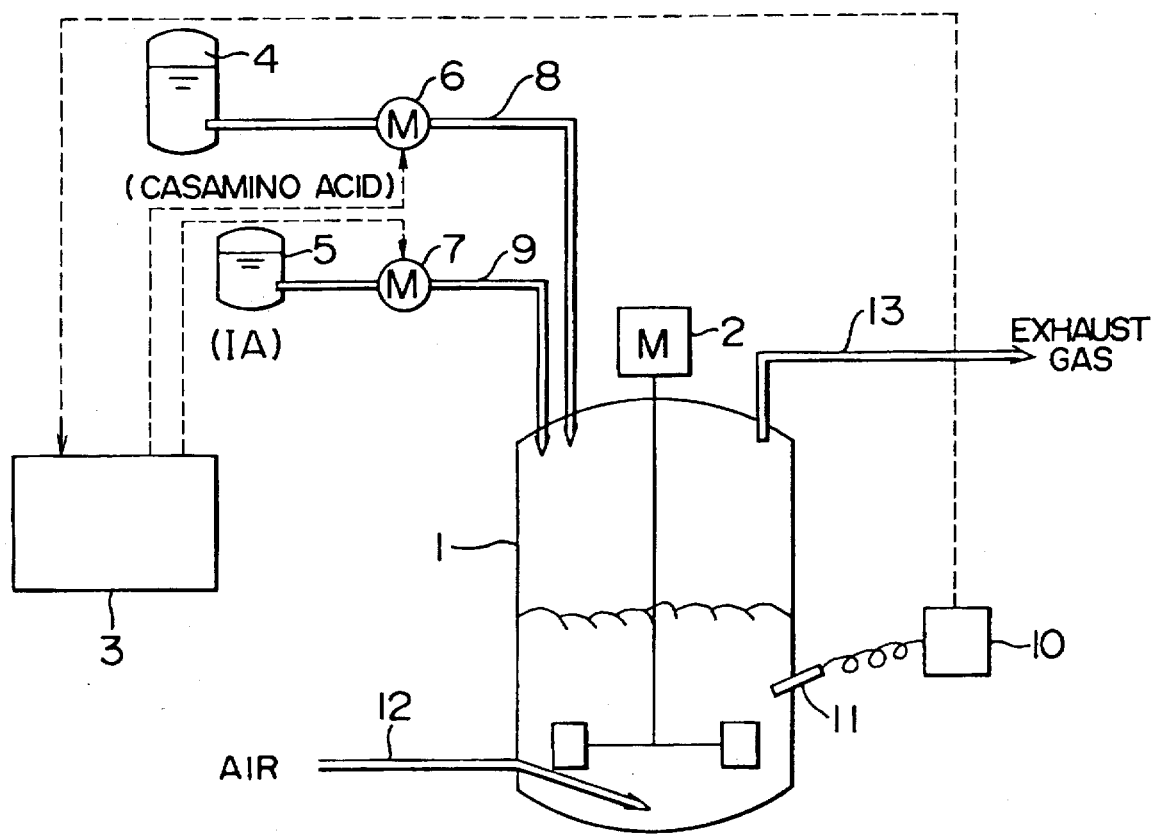
FIG. 5 is a schematic diagram showing one example of culture apparatus usable in this invention.

FIG. 5 shows one example of apparatus suitable for practicing the present invention. In FIG. 5, a culture medium and seed microorganism are placed in a culture tank 1, wherein a recombinant is cultivated while blowing air into the culture tank 1 through a pipe 12 and stirring a culture solution with a stirrer 2. The dissolved oxygen concentration of the culture solution is measured by using a dissolved oxygen sensor 11 step up to the culture tank 1 and a dissolved oxygen meter 10. The measured data are input to an electronic computer for controlling 3 to watch the change of dissolved oxygen concentration. When the dissolved oxygen concentration increases rapidly, signals are input to fixed displacement pumps 6 and 7 so as to supply a nutriment such as casamino acid from a substrate tank 4 and an inducer such as IA from an adding tank 5 in predetermined amounts at the same time to the culture tank 1. The cultivation is continued for a predetermined time, the microorganisms in the culture solution are recovered, and the desired useful substance such as β-galactosidase produced in the microorganisms is separated and purified. In FIG. 5, numerals 8 and 9 are pipes.

As a means for consuming the nutriment present in the culture medium from the beginning, it is possible to add a repressing substance to the culture medium at the initial stage of the culture. That is, the expression of genes is controlled by a gene region called a "promoter-operator". In the case of trp promoter, an RNA polymerase is linked to a trp promoter and transferred to the downstream of the promoter to transcript the DNA base sequence so as to synthesize RNA. And a polypeptide is synthesized by translation of the information of the synthesized RNA by a ribosome.

On the other hand, when the tryptophan concentration in a cell increases, tryptophan is linked to a repressor to activate it, and the repressor is linked to a region called an "operator". As a result, the RNA polymerase cannot be linked to the promoter portion. The production of polypeptide terminates due to no synthesis of RNA. In such a case, tryptophan acts as a repressing substance. This invention also provides a process for producing a polypeptide, e.g., β-galactosidase, effectively by applying the gene expression control in the trp promoter.

For example, when E. coli M182 containing hybrid plasmid pTREZ1 deposited in the FRI as FERM BP-816 is cultivated in a culture medium containing a trace of or no tryptophan, for example, in a M9-casamino acid culture medium, β-galactosidase is produced from the initial stage of culture. In such a case, since the multiplication of the microorganisms is little, the produced amount of β-galactosidase per culture solution is low.

In order to increase the produced amount of β-galactosidase, a small amount of tryptophan which is a repressing substance is added at the initial stage of culture to suppress the action of trp promoter and to lower the production of β-galactosidase so as to multiply the microorganisms. The amount of tryptophan to be added is preferably 2.5 to 10 μg/ml, more preferably about 5 μg/ml. When the content of nutriment in the culture medium is remarkably lowered or becomes zero, an inducer such as IA which initiates the action of trp promoter is added to the culture solution together with a nutriment so as to activate the trp promoter and so as to make E. coli utilize the nutriment added to the culture solution. Thus, β-galactosidase is produced in large amounts.

The culture process applying the trp promoter expression controlling mechanism and attaining separately the microorganism multiplication and the β-galactosidase production is not known in this art.

This invention is illustrated by way of the following Examples.

EXAMPLE 1

Microorganism: E. coli M182 containing hybrid plasmid pTREZ1

Culture medium: M9-casamino acid culture medium (NH$_4$Cl 1 g, Na$_2$HPO$_4$ 6 g, KH$_2$PO$_4$ 3 g, NaCl$_5$ g, MgSO$_4$.7H$_2$O 0.1 g, CaCl$_2$.2H$_2$O 15 mg, glucose 5 g, casamino acid 2.5 g, distilled water 1 liter, pH 7.0). In order to multiply only E. coli M182 containing plasmid pTREZ1, 50 μg/ml of ampicillin (Ap) was added to the culture medium.

Culture conditions: E. coli M182 containing plasmid pTREZ1 was inoculated into 100 ml of M9-casamino acid culture medium placed in 20 shaking flasks having a working volume of 500 ml and incubated overnight at 37° C. using a shaking incubator at 115 oscillations per minute with a 7-cm stroke. The cultivated microorganisms are recovered by centrifugation and suspended in 50 ml of the M9-casamino acid culture medium. It was inoculated into 2 liters of M9-casamino acid culture medium in 5-liters jar fermenter as seed microorganisms to start the culture. Two drops of antifoam agent solution (Lion Co., Ltd., 1705-W) were added. The culture was conducted at a temperature of 37° C. and pH 7.2, with the agitation speed of 800 r.p.m., and air flow rate of 2 liters/min for 6 hours.

Figure 6:
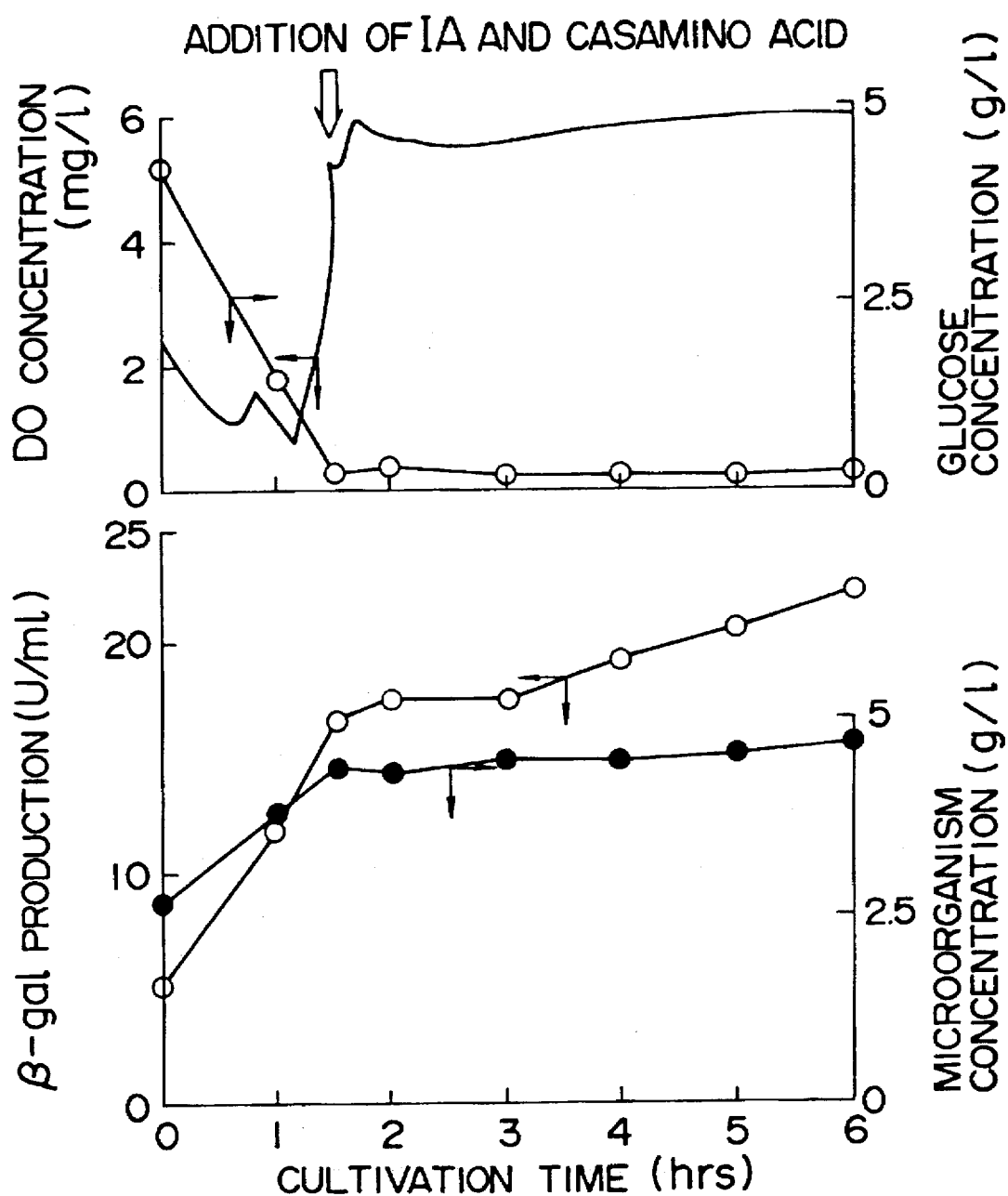
FIG. 6 is a graph showing an influence of adding time of IA and casamino acid using a DO concentration as an indicator.

Results:

Since the dissolved oxygen (DO) concentration was rapidly increased after about 1.5 hours' culture as shown in FIG. 6, 15 μg/ml of IA and 2.5 mg/ml of casamino acid were added simultaneously. The β-galactosidase produced amount at the time of simultanoeus addition of IA and casamino acid was 16.6 U/ml, but increased to 21.8 U/ml which value is about 1.3 times as large as the value of 16.6 U/ml after 6 hours' culture. After the addition of IA and casamino acid, the microorganism concentration hardly increased; this seems that almost all the casamino acid added is consumed for the production of β-galactosidase.

From the above-mentioned results, it becomes clear that the β-galactosidase produced amount can remarkably be increased by the simultaneous addition of IA and casamino acid using the DO concentration as an indicator.

COMPARATIVE EXAMPLE 1

Microorganism: the same as Example 1
Culture medium: the same as Example 1
Culture conditions:

The procedures of Example 1 were repeated except for adding only 2.5 mg/ml of casamino acid at the time of increase of the DO concentration.

Figure 7:
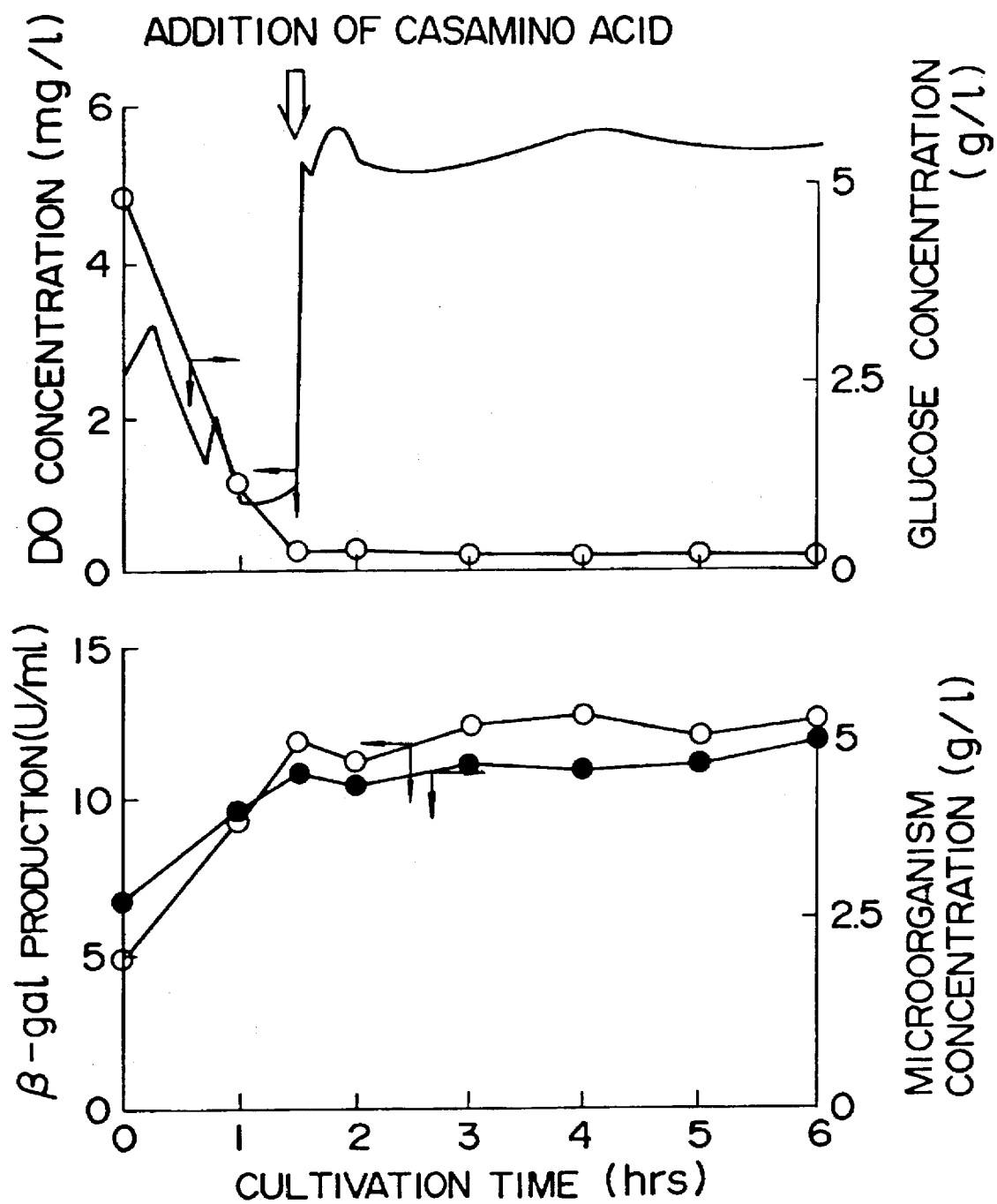
FIG. 7 is a graph showing an influence of adding time of casamino acid using a DO concentration as an indicator.

Results:

Since the DO concentration was rapidly increased after about 1.5 hours' culture as shown in FIG. 7, 2.5 mg/ml of casamino acid alone was added to the culture solution. In this case, the β-galactosidase produced and the microorganism concentration were hardly increased after the addition of casamino acid. This means that the addition of IA is necessary for improving the production of β-galactosidase.

EXAMPLE 2

On a plate of L-broth culture medium (tryptone 10 g, yeast extract 5 g, glucose 1 g, NaCl 5 g, city water 1 liter, pH 7.2) containing 50 μg/ml of ampicillin, E. coli M182 containing plasmid pTREZ1 (deposited in the FRI as FERM BP-816) was plated out. A part of colony produced was inoculated into 50 ml of culture solution obtained by adding 50 μg/ml of ampicillin to M9-casamino acid culture medium (NH$_4$Cl 1 g, Na$_2$HPO$_4$ 6 g, KH$_2$PO$_4$ 3 g, NaCl 5 g, MgSO$_4$.7H$_2$O 0.1 g, CaCl$_2$.2H$_2$O 15 mg, glucose 5 g, casamino acid 2.5 g, distilled water 1 liter, pH 7.0) placed in a shaking flask with a cotton plug. The culture was carried out at 37° C. while shaking at 120 oscillations per minutes for 15 hours. After the stoppage of the culture, the resulting solution was subjected to centrifugation with 10000 r.p.m. for 5 minutes. The collected microorganisms were suspended in the above-mentioned M9-casamino acid culture medium and placed in three shaking flasks with a cotten plug in an amount of 50 ml. To these shaking flasks, tryptophan was added in amounts of 2.5 μg/ml, 5 μg/ml and 10 μg/ml, respectively. On the other hand, the same culture medium as mentioned above except for adding no tryptophan was placed in a shaking flask for comparison. After the addition of tryptophan or no addition of tryptophan, the culture was carried out at 37° C. with shaking at 120 oscillations per minute for 2 hours, and then 15 μg/ml of IA and 2.5 mg/ml of casamino acid as a nutriment were added, followed by the culture for additional 3 hours.

After the culture, each 1 ml of culture medium was added 15 μl of toluene and shaked at 37° C. for 30 minutes. After shaking, the culture medium was diluted 10 to 100 times in order to measure the produced amount of β-galactosidase. One ml of the solution was taken out and shaked at 30° C. for 5 minutes, followed by addition of 3.5 ml of 0.2M phosphate buffer (pH 7.25) and 0.5 ml of 0.01M O-nitrophenyl-β-D-galactopyranoside (ONPG) and 10 minutes' shaking. After sampling 1 ml of the solution and stopping the reaction by placing it in 1M Na$_2$CO$_3$, 8 ml of water was added thereto so as to make the whole amount 10 ml. The absorbance of this sample was measured at 420 nm by using a spectrophotometer. The amount of O-nitrophenol (ONP) produced was calculated from the standard curves of ONT. In this case, the β-galactosidase activity for decomposing 1 μmole of ONPG per minute was defined as one unit (U).

Figure 8:
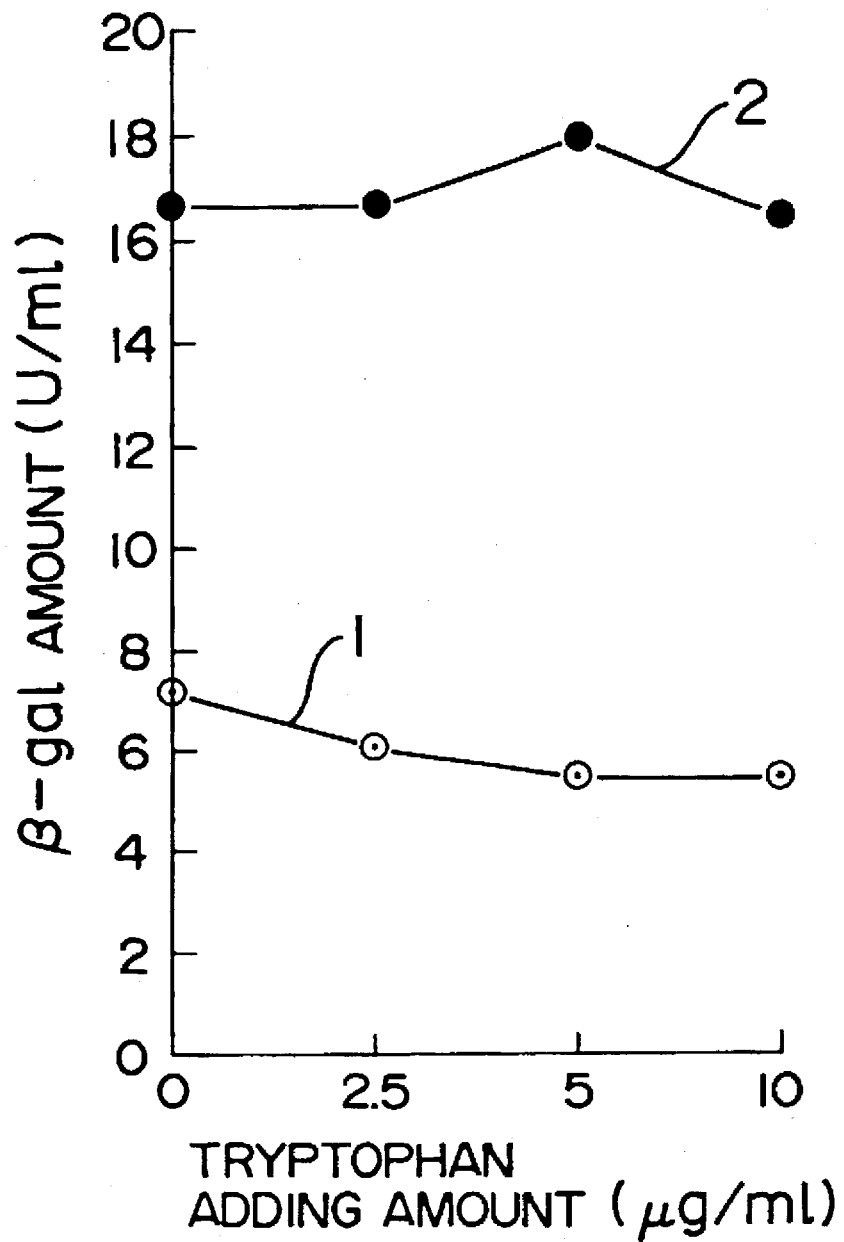
FIG. 8 is a graph showing a relationship between the amount of tryptophan and the β-galactosidase produced.

The results are shown in FIG. 8. At 2 hours from the beginning of culture (curve 1), the β-galactosidase produced amount is decreased with an increase of the adding amount of tryptophan, since the action of trp promoter is suppressed by the addition of tryptophan. But as shown in the curve 2 wherein IA and casamino acid are added after 2 hours' culture followed by 3 hours' additional culture, the β-galactosidase produced shows a maximum value at the addition of 5 μg/ml of tryptophan, the value being 10% as large as the case of adding no tryptophan.

As mentioned above, the addition of tryptophan which is a repressing substance for a trp promoter at an initial stage of the culture, followed by the addition of an inducer and a nutriment at the time when almost the nutriment initially present in the culture medium is consumed, is effective for remarkably improving the production of β-galactosidase.

According to this invention, the suppression and induction of the production of desired products can be conducted as desired in the culture of recombinants, and thus industrial production of the desired products by using the microorganisms harboring hybrid plasmids can be carried out with high efficiency.

What is claimed is:

1. A process for increasing the production of β-galactosidase by a culture of E. coli comprising the steps of:

a) adding a culture of E. coli having a pTREZ1 hybrid plasmid containing a tryptophan promoter and a β-galactosidase gene to a first medium for cultivation, wherein said first medium contains an initial growth supporting level of glucose;

b) adding oxygen to said first medium to promote the multiplication of the E. coli, wherein said oxygen is added to the first cultivation medium at a constant flow rate;

c) monitoring the dissolved oxygen concentration of the first cultivation medium; and, d) adding simultaneously 3-β-indolylacrylic acid and a second medium containing casamino acid to the first cultivation medium at a time when the dissolved oxygen concentration of said first cultivation medium changes from a decrease to an increase.

2. A process for increasing the production of β-galactosidase by a culture of E. coli comprising the steps of:

a) adding a culture of E. coli having a pTREZ1 hybrid plasmid containing a tryptophan promoter and a β-galactosidase gene to a first medium for cultivation, wherein said first medium contains an initial growth supporting level of glucose;

b) adding tryptophan to the first cultivation medium, wherein said tryptophan suppresses the production of β-galactosidase by the E. coli;

c) adding oxygen to said first medium to promote the multiplication of the E. coli, wherein said oxygen is added to the first cultivation medium at a constant flow rate;

d) monitoring the dissolved oxygen concentration of the first cultivation medium; and, e) adding simultaneously 3-β-indolylacrylic acid and a second medium containing casamino acid to the first cultivation medium at a time when the dissolved oxygen concentration of said first cultivation medium changes from a decrease to an increase.

3. The process of claim 1, wherein said E. coli is selected from the group consisting of E. coli M182, E. coli HB101, E. coli C600, E. coli X1776, and E. coli DH1.

4. The process of claim 2, wherein said E. coli is selected from the group consisting of E. coli M182, E. coli HB101, E. coli C600, E. coli X1776, and E. coli DH1.

5. A process for increasing the production of β-galactosidase by a culture of E. coli comprising the steps of:

a) adding E. coli M182 having a pTREZ1 hybrid plasmid containing a tryptophan promoter and a β-galactosidase gene to a first medium for cultivation, wherein said first medium contains an initial growth supporting level of glucose;

b) adding oxygen to said first medium to promote the multiplication of the E. coli, wherein said oxygen is added to the first cultivation medium at a constant flow rate;

c) monitoring the dissolved oxygen concentration of the first cultivation medium; and, d) adding simultaneously 3-β-indolylacrylic acid and a second medium containing casamino acid to the first cultivation medium at a time when the dissolved oxygen concentration of said first cultivation medium changes from a decrease to an increase.

6. A process for increasing the production of β-galactosidase by a culture of E. coli comprising the steps of:

a) adding a culture of E. coli M182 having a pTREZ1 hybrid plasmid containing a tryptophan promoter and a β-galactosidase gene to a first medium for cultivation, wherein said first medium contains an initial growth supporting level of glucose;

b) adding tryptophan to the first cultivation medium, wherein said tryptophan suppresses the production of β-galactosidase by the E. coli;

c) adding oxygen to said first medium to promote the multiplication of the E. coli, wherein said oxygen is added to the first cultivation medium at a constant flow rate;

d) monitoring the dissolved oxygen concentration of the first cultivation medium; and, e) adding simultaneously 3-β-indolylacrylic acid and a second medium containing casamino acid to the first cultivation medium at a time when the dissolved oxygen concentration of said first cultivation medium changes from a decrease to an increase.

* * * * *